United States Patent [19]

Vogt et al.

[11] 4,130,592
[45] Dec. 19, 1978

[54] METHOD FOR THE PREPARATION OF CHLOROACETALDEHYDEDIMETHYL ACETAL

[75] Inventors: Wilhelm Vogt, Koeln-Suelz; Herman Richtzenhain, Post Marialinden, both of Germany

[73] Assignee: Dynamit Nobel Aktiengesellschaft, Troisdorf Bez. Koeln, Germany

[21] Appl. No.: 336,286

[22] Filed: Feb. 27, 1973

Related U.S. Application Data

[63] Continuation of Ser. No. 182,861, Sep. 22, 1971, abandoned, which is a continuation-in-part of Ser. No. 169,494, Aug. 5, 1971, Pat. No. 3,784,612, which is a continuation-in-part of Ser. No. 774,216, Nov. 7, 1968, abandoned.

[30] Foreign Application Priority Data

Nov. 11, 1967 [DE] Fed. Rep. of Germany ....... 1643899
Mar. 16, 1968 [DE] Fed. Rep. of Germany ....... 1693017

[51] Int. Cl.$^2$ ..................... C07C 41/00; C07C 43/30; C07C 41/10
[52] U.S. Cl. ....................................... 568/604; 568/681
[58] Field of Search ......................... 260/615 A, 614 R

[56] References Cited

U.S. PATENT DOCUMENTS

| 2,247,482 | 7/1941 | Dickey et al. | 260/615 A |
| 2,481,157 | 9/1949 | Schmerling | 260/615 A |
| 2,550,637 | 4/1951 | Copenhaver | 260/615 A |
| 2,803,668 | 8/1957 | Morris et al. | 260/615 A |
| 3,426,035 | 2/1969 | Bremmer | 260/650 R X |

FOREIGN PATENT DOCUMENTS

| 1592333 | 6/1970 | France | 260/615 A |
| 249039 | 3/1926 | United Kingdom | 260/615 A |
| 418230 | 10/1934 | United Kingdom | 260/652.5 |

OTHER PUBLICATIONS

Kobayashi et al., Chem. Abst. 53 1156$^h$ 1959.
Karrer, Organic Chemistry, Elsevier Publishing Co., New York, Second English Ed., 1946 p.231.

Primary Examiner—Howard T. Mars
Attorney, Agent, or Firm—Sprung, Felfe, Horn, Lynch & Kramer

[57] ABSTRACT

Production of chloroacetaldehydedimethyl acetal by the reaction of a vinyl halide with chlorine and methanol in contact with an acid binding material in an approximately anhydrous system. Co-produced dichloroethyl, methyl ether is also disclosed.

8 Claims, No Drawings

METHOD FOR THE PREPARATION OF CHLOROACETALDEHYDEDIMETHYL ACETAL

This is a continuation of application Ser. No. 182,861, filed Sept. 22, 1971, now abandoned, which, in turn, is a contination-in-part of copending application Ser. No. 169,494, filed Aug. 5, 1971, now U.S. Pat. No. 3,784,612, which, in turn is a continuation of Ser. No. 774,216 filed Nov. 7, 1968, now abandoned.

This invention relates to chloroacetaldehydedimethyl acetal. It more particularly refers to a novel and improved method of producing such.

Acetals and ketals of α-chlorinated aldehydes and ketones can be obtained from their respective chlorinated aldehydes or ketones, as the case may be, by reacting them with alcohols according to methods commonly used for the preparation of non-chlorinated acetals and ketals. In these processes the aldehyde or ketone is made to react with excess alcohol in the presence of acid catalysts, with the simultaneous azeotropic removal of the reaction water. It is furthermore known that acetals of α-chlorinated aldehydes can be prepared from the corresponding chloroaldehydes and alcohols in the presence of catalytically active water-soluble salts of Main Groups II and III, and of Sub-Groups II, VI, VII or VIII of the periodic system, or of ammonium, also with the use of stoichiometric amounts of alcohol.

All of these methods start from the premise that α-chlorinated aldehydes and ketones are available as starting materials. Often such aldehydes or ketones are not easily accessible, and frequently even when they are accessible, they can be handled only with certain special precautions because of their intense irritant action.

Methods have also been described in which acetals of chloroaldehydes are prepared by the chlorination of acetals or of vinyl ethers and/or vinyl esters in the presence of methanol. These methods, however, have been found to be difficult to apply on an industrial scale.

It has now surprisingly been found, that one of these α-chlorinated acetals, the most important one industrially, chloroacetaldehydedimethyl acetal, can be prepared in a considerably simpler fashion and from physiologically less hazardous reactants by reacting a vinyl chloride with chlorine and methanol and neutralization of the reaction mixture with an acid binding material. It is preferred that the reaction be carried out with a hyperstoichiometric amount, that is at least 100% excess, of methanol containing less than 2% of weight of water. When reacting vinylchloride with Cl$_2$ and methanol, two different reactions take place, i.e. a chloroalkoxylation of the vinylchloride and a chlorine addition to vinylchloride. With the chloroalkoxylation of the vinylchloride, 1,2-dichloro-1-methoxyethane is formed as main product, which as an α chlorinated ether with an excess of methanol is reacting to chloroacetaldehydedimethylacetal.

The 2,2-dichloroethyl-methylether, not having been known up to now, is formed as by-product of the chloroalkoxylation. The formation of these products take place according to the following formula:

$$CH_2=CHCL + CH_3OH + Cl_2$$

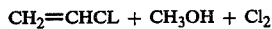

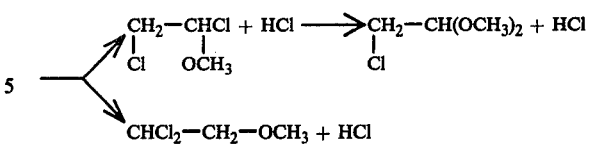

$$CHCl_2-CH_2-OCH_3 + HCl$$

Furthermore, 1,1,2 trichloroethane is formed by adding chlorine to vinylchloride.

The quantity of the 2,2-dichloroethylmethylether formed, is substantially independent from the conditions of the reaction and amounts to approx. 11% relative to the amount of the chloroacetaldehydedimethylacetal.

The quantity of the formed 1,1,2-trichloroethane depends on the ratio of the amounts of methanol and chlorine and thus on the concentration of Cl-ions contained in the reaction mixture and on the reaction temperature. By using a large excess of methanol or by removing the Cl-ions, which are formed during the reaction with acid binding reagents, it is possible to direct the reaction substantially in favour of the formation of the chloroacetaldehydedimethylacetal and the quantity of 1,1,2-trichloroethane can be kept low. With a mole ratio of methanol:chlorine of 10:1, the amount of 1,1,2-trichloroethane formed, is 28.5 mole %, whereas with a mole ratio of 5:1 the amount of 1,1,2 trichloroethane formed, is 43.2 mole %. The preferred range is a molar ratio of at least 8 mole of methanol per mole of chlorine resp. vinyl chloride.

The reaction takes place in the alcoholic solution at temperatures between −20° C. and 100° C., advantageously at temperatures between −20° C. and 30° C., most advantageously at 0 ° to 30° C.

The speed of the reaction depends on the concentration of the vinyl chloride and chlorine in the reaction mixture, and on the apparatus used in performing the reaction. To prevent a momentary overconcentration, it is desirable to feed the chlorine into the reaction mixture, controlling the rate of introduction advantageously in such a manner that it corresponds approximately to the rate at which the reaction mixture absorbs the chlorine. For the achievement of the highest possible yield, the vinyl halide is reacted with chlorine advantageously in a molar ratio of 1:1, a slight excess of 1-2% of vinyl chlorine is of advantage.

In case the Cl-ions developing in the course of the chloroalkoxylation are continuously removed, the formation of the 1,1,2-trichloroethane is considerably repressed and then nearly independent of the methanol-chlorine-ratio. The methanol used for the reaction has to be substantially free of water. At a water content of >2% the formation of free chloroacetaldehyde takes place by means of hydrolysis of the initially developed 1,2-dichloro-1-methoxyethane. This free chloroacetaldehyde which can be titrated with bisulfite leads to undesired polymerization and cracking in the distillation columns when the distillations necessary to isolate the pure acetal are carried out. It is thus preferred to use methanol having a water content of <0.8%.

The method of the present invention can be practiced with the addition of acid-binding reagents such as the hydroxides, oxides, carbonates and alcoholates of metals of Main Groups I and II of the Periodic Table. Particularly suitable are the hydroxides, oxides, carbonates and alcoholates of potassium, sodium, magnesium and calcium. The acid binding reagents named are used preferably in stoichiometric amounts, although they can also be used in a smaller quantity than that called for by the stoichiometric ratio. The use of alkali metal compounds as acid binding reagents is particularly advantageous because the resulting alkali chlorides are difficultly soluble in the reaction medium. The solubility of sodium chloride in methanol at 20° C. is less than 1.5% by weight. Due to their poor solubility the compounds are also easy to remove from the reaction mixture.

The acid binding reagents can also be aliphatic compounds having one or more 1,2-epoxide groups, i.e., aliphatic 1,2-epoxides of the monoepoxide type, as well as polyepoxides. Suitable monoepoxides are the epoxidized compounds of monounsaturated hydrocarbons (ethylene, propylene, butylene, cyclohexene), halogen-containing epoxides (epichlorhydrin) and glycide ethers of univalent alcohols (methyl, ethyl, n- and i-propyl, n-, i- and tert. butyl, 2-ethyl hexyl and dodecyl alcohol etc.). Examples of suitable polyepoxides are: epoxides of poly-unsaturated hydrocarbons (vinylcyclohexene, dicyclopentadiene, cyclo-hexadiene, cyclododecatriene, butadines) and glycidyl ethers of polyvalent alcohols (ethylene, propylene and butylene glycols, polyglycols, thiodiglycols, glycerin, etc.). The aliphatic 1,2-epoxides are used preferably in stoichiometric quantities, i.e. 1 mole of monoepoxide per mole of chlorine, 0.5 mole of diepoxide per mole of chlorine, etc. However, they can also be used in excess without affecting the yield. A slight excess (2–5%) above the stoichiometric ratio has proven advantageous.

The acid binding agents used to neutralize the acid that develops in the reaction can be used either in solid form, in solution, or in suspension.

The reaction of the vinyl chloride with chlorine in methanol is performed by introducing the chlorine and the vinyl chloride continuously into the methanol reaction medium — preferably separately — in the same molar ratio. The addition of the acid binding reagent can also be performed continuously. The neutralization of the reaction solution, however, can alternatively be performed after the reaction has ended. The methanol is used generally in a 8 to 30-fold molar excess. the $\alpha$-chloroacetaldehyde dimethyl acetal prepared by this process can be used as insecticide and as valuable intermediates for the manufacture of a number of products, such as 1,1,2-trimethoxy ethane or 2-amino thiazol.

The process of the present invention is illustrated by the following examples:

EXAMPLE 1

Over a period of 4.8 hours, 125 g of vinyl chloride (2 moles) were introduced into 640 g of methanol and at the same time 2 moles of chlorine were fed in at a rate of 9.3 l/h (molar ratio chlorine to methanol 1:10). The reaction temperature was maintained during this period at 0° to 5° C. After the end of the reaction, the mixture was neutralized with sodium methylate and the precipitated sodium chloride was filtered out. The gas chromatography showed, for a vinyl chloride transformation of 85%, 63.6 wt-% of chloroacetaldehydedimethylacetal 7.9% 2,2-dichloroethylmethylether and 28.5 wt-% of 1,1,2-trichloroethane.

EXAMPLE 2

Over a period of 9.6 hours, 250 g of vinyl chloride (4 moles) were introduced into 640 g of methanol (20 moles) and at the same time 4 moles of chlorine were fed in at a rate of 9.3 l/h (molar ratio chlorine to methanol 1:5). The reaction temperature was maintained at 0° to 5° C. during this period. After the reaction had ended, the mixture was neutralized with sodium methylate and the precipitated sodium chloride was removed by filtration. At a vinyl choride transformation of 83%, the gas chromatography indicated 50.6 wt-% of chloroacetaldehydedimethylacetal 6.2% 2,2-dichloroethylmethylether and 43.2 wt.-% of 1,1,2-trichloroethane.

EXAMPLE 3

114 g of ethylene oxide (3 moles) was added to 320 g of methanol (10 moles). Over a period of 3.5 hours, 62.5 g of vinyl chloride (1 mole) was added to this reaction solution, and at the same time 1 mole of chlorine was fed in at a rate of 6.5 l/h (molar ratio chlorine to methanol 1:10). The reaction temperature was maintained at 0°–5° C. during this period. After the end of the reaction, a small remainder of the hydrochloric acid that had not been intercepted by the ethylene oxide was neutralized with sodium methylate and the mixture was filtered free of sodium chloride. At a vinyl chloride transformation of 91.6%, the gas chromatography showed a ratio of chloroacetaldehydedimethylacetal to 2,2-dichloroethylmethylether to 1,1,2-trichloroethane of 82.7:10.3 : 7 percent by weight.

EXAMPLE 4

In the course of 3.5 hours, 62.5 g of vinyl chloride (1 mole) was introduced into 160 g of methanol (5 moles), and 1 mole of chlorine was simultaneously introduced at a rate of 6.5 l/h (molar ratio chlorine to methanol 1:5). The reaction temperature was maintained during this period at 0° to 5° C. After the reaction had ended, the mixture was neutralized with sodium methylate and precipitated sodium chloride was removed by filtration. At a vinyl chloride transformation of 83.5%, the gas chromatography showed a ratio of chloroacetaldehydedimethylacetal to 2,2-dichloroethylmethylether to 1,1,2-trichloroethane of 55.6:6.19:37.5 percent by weight.

EXAMPLE 5

57 g ethylene oxide (1.5 moles) were added to 160 g of methanol (5 moles). 62.5 g of vinyl chloride (1 mole) was introduced into this reaction solution over a period of 3.5 hours, simultaneously with 1 mole of chlorine which was fed in at a rate of 6.5 l/h (molar ratio chlorine to methanol 1:5). The reaction temperature was maintained during this period at 0° to 5° C. After the reaction had ended, the remainder of unreacted hydrochloric acid was neutralized with sodium methylate and the sodium chloride was removed by filtration. At a vinyl chloride transformation of 88%, gas chromatography showed a ratio of chloroacetaldehydedimethylacetal to 2,2-dichloroethylmethylether to 1,1,2-trichloroethane of 79.5:9.8:10.7 percent by weight.

EXAMPLE 6

Over a period of 3.5 hours, 62.5 g of vinyl chloride (1 mole) was introduced into 160 g of methanol (5 moles), and 1 mole of chlorine was simultaneously introduced at a rate of 6.5 l/h (molar ratio chlorine to methanol 1:5), at a reaction temperature of 0° to 5° C. The hydrochloric acid that formed in the reaction was continously neutralized with sodium methylate. After the reaction had ended the sodium chloride was filtered out and the organic solution was neutralized. At a vinyl chloride transformation of 88% the gas chromatography showed a ratio of chloroacetaldehydedimethylacetal to 2,2- dichloroethylmethylether to 1,1,2-trichloroethane of 79.5:9.8:10.7 percent by weight.

What is claimed is:

1. In the process of producing chloroacetaldehydedimethylacetal and 2,2-dichloroethylmethylether which comprises reacting vinyl chloride with chlorine and methanol at a temperature between −20° C. and 100° C., the improvement which comprises carrying out the reaction in the presence of a stoichiometric amount, based on the amount of HCl formed in the process, of an HCl acid binding material selected from the group consisting of aliphatic 1,2-epoxides, hydroxides, oxides, carbonates and alcoholates, of elements of the first and second sub-group of the Periodic Table, ammonia, amines and basic ion exchange resins, said methanol containing less than 2% by weight water, and being present in a molar excess with respect to said chlorine and neutralizing the reaction mixture by addition of an acid binding material.

2. Process claimed in claim 1 wherein said reaction is carried out at +5° to 25° C.

3. Process claimed in claim 1 wherein said reaction is carried out at −20° to +30° C.

4. A process according to claim 3 wherein the acid binding agent is an epoxide and is present in an excess of between 2 and 5% above the stoichiometric amount and the acid binding agent is added to the reaction mixture continuously.

5. A process according to claim 4 wherein the reaction of the vinyl chloride with chlorine and methanol is performed by introducing the chlorine and the vinyl chloride continuously into the methanol reaction medium and the methanol is present in an eight- to thirtyfold molar excess.

6. A process according to claim 1 wherein the acid binding reagent is selected from the group consisting of sodium hydroxide, magnesium hydroxide, calcium hydroxide, sodium oxide, magnesium oxide, calcium oxide, sodium carbonate, magnesium carbonate, calcium carbonate, potassium hydroxide, potassium oxide, potassium carbonate, potassium alcoholate, magnesium alcoholate, calcium alcoholate, sodium alcoholate, ethylene monoepoxide, propylene monoepoxide, butylene monoepoxide, cyclohexene monoepoxide, epichlorhydrin, the glycide ether of methanol, the glycide ether of ethanol, the glycide ether of normal propanol, the glycide ether of isopropanol, the glycide ether of isobutanol, the glycide ether of tert. butanol, the glycide ether of 2-ethylhexanol, the glycide ether of dodecyl alcohol, the epoxide of vinylcyclohexene, the epoxide of dicyclopentadiene, the epoxide of cyclo-hexadiene, the epoxide of cyclododecatriene, a polyepoxide of a butadiene, the glycidyl ether of ethylene glycol, the glycidyl ether of propylene glycol, the glycidyl ether of a butylene glycol, the glycidyl ether of a polyglycol, the glycidyl ether of a thiodiglycol, and the glycidyl ether of glycerin.

7. Process according to claim 4 wherein the vinyl halide is reacted with the chlorine such that there is an excess of between 1 and 2 percent of vinyl chloride over the stoichiometric amount.

8. A process according to claim 1 wherein the molar ratio of methanol to chlorine is 10:1.

* * * * *